(12) United States Patent
Ilic

(10) Patent No.: US 6,685,717 B1
(45) Date of Patent: Feb. 3, 2004

(54) SCALPEL SYSTEM FOR TREATING CARPAL TUNNEL SYNDROME

(75) Inventor: Sergio Ilic, Fresno, CA (US)

(73) Assignee: floVector, L.L.C., Fresno, CA (US)

( * ) Notice: Subject to any disclaimer, the term of this patent is extended or adjusted under 35 U.S.C. 154(b) by 0 days.

(21) Appl. No.: 09/930,839

(22) Filed: Aug. 15, 2001

(51) Int. Cl.$^7$ .............................................. A61B 17/32
(52) U.S. Cl. ...................................... 606/167; 606/170
(58) Field of Search ................................ 606/167, 166, 606/170, 172; 30/49, 340, 342, 343

(56) References Cited

U.S. PATENT DOCUMENTS

| | | | |
|---|---|---|---|
| 4,962,770 A | * 10/1990 | Agee et al. .................. | 128/898 |
| 5,029,573 A | * 7/1991 | Chow .......................... | 600/104 |
| 5,269,796 A | * 12/1993 | Miller et al. ................. | 606/167 |
| 5,306,284 A | * 4/1994 | Agee et al. .................. | 606/170 |
| 5,323,765 A | * 6/1994 | Brown ......................... | 600/104 |
| 5,334,214 A | 8/1994 | Putnam | |
| 5,387,222 A | 2/1995 | Strickland | |
| 5,413,580 A | 5/1995 | Stephenson | |
| 5,507,800 A | 4/1996 | Strickland | |
| 5,649,946 A | 7/1997 | Bramlet | |
| 5,769,865 A | 6/1998 | Kermode et al. | |
| 2002/0099399 A1 | * 7/2002 | Lee et al. .................... | 606/167 |

OTHER PUBLICATIONS

"Carpal Tunnel Syndrome Decompression using the Paine retinaculatome," Paine KWI, Polyzoidis KA; Journal of Neurosurgery 59:1031–1036, 1983.*

Pagnanelli and Barrer, "Carpal tunnel syndrome: surgical treatment using the Paine retinaculatome," *J. Neurosurg.*, 75, pp. 77–81, Jul. 1991.

"Overview of Carpal Tunnel Syndrome," http://www.biomet.com/extremities/carpal/overview.cfm, viewed Dec. 22, 1997.

"Common Methods of Treating Carpal Tunnel Syndrome," http://www.biomet.com/extremities/carpal/treat.cfm, viewed Dec. 22, 1997.

"'Minimally Open' Carpal Tunnel Release Surgical Technique," http://www.biomet.com/extremities/security.cfm, viewed Dec. 22, 1997.

"Carpal Tunnel Release System The Indiana Tome™, " http://www.biomet.com/carpal/index.cfm, viewed Dec. 22, 1997.

"Safeguard™ Mini Carpal Tunnel Release System"; 6 pages—description and illustrations; KMI Incorporated [company marketing publication], 4114 Sorrento Valley Blvd., San Diego, California, 92121.

* cited by examiner

Primary Examiner—Julian W. Woo
Assistant Examiner—Bradford C Pantuck
(74) Attorney, Agent, or Firm—Parsons Hsue & de Runtz LLP

(57) ABSTRACT

A surgical instrument for relieving carpal tunnel syndrome has an elongated member including a first portion for handling and a second portion. The second portion has a first surface, a second surface, and a blade on the first surface. The blade has a trailing edge and a sharp, convex leading edge. The leading edge rises gradually at a first angle with respect to the first surface so that when the leading edge is pushed against tissue to make an incision, damage to the surrounding tissue is reduced. The first angle is less than 90 degrees. In carpal tunnel release surgery, a transverse incision is made in the patient's distal wrist crease with a surgical instrument. The surgical instrument is positioned below the, transverse carpal ligament and advanced in a closed procedure towards the patent's fingertips until the transverse carpal ligament is completely transected.

23 Claims, 2 Drawing Sheets

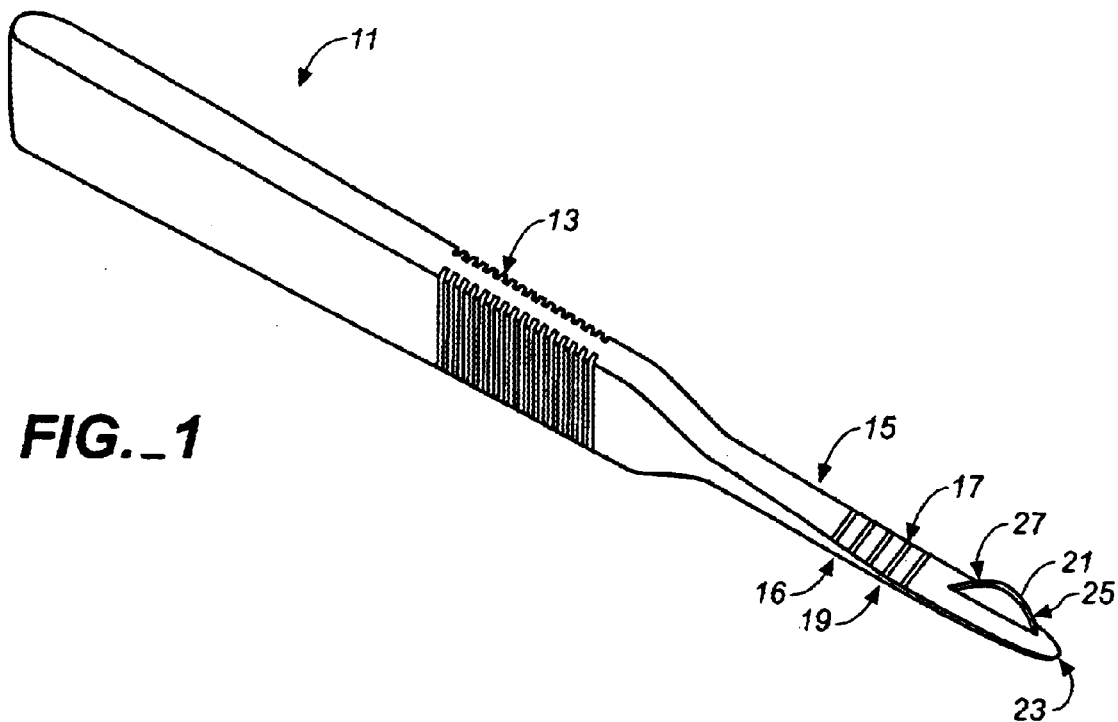
FIG._1
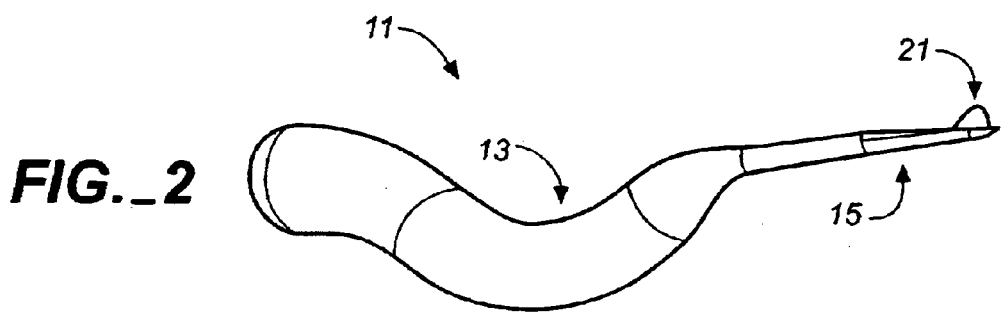
FIG._2
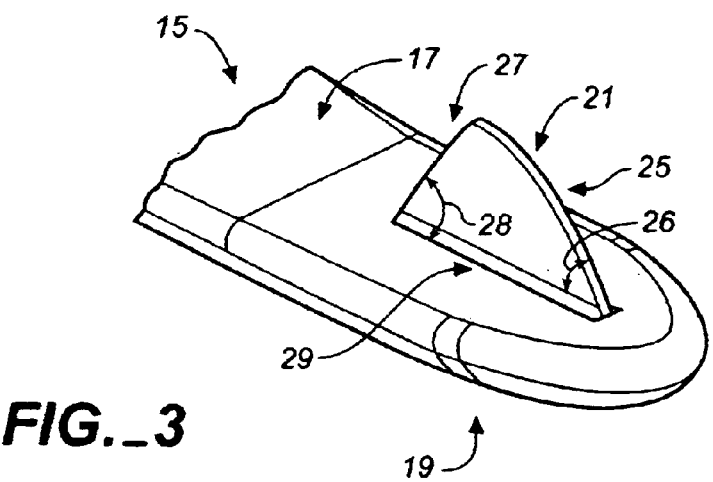
FIG._3

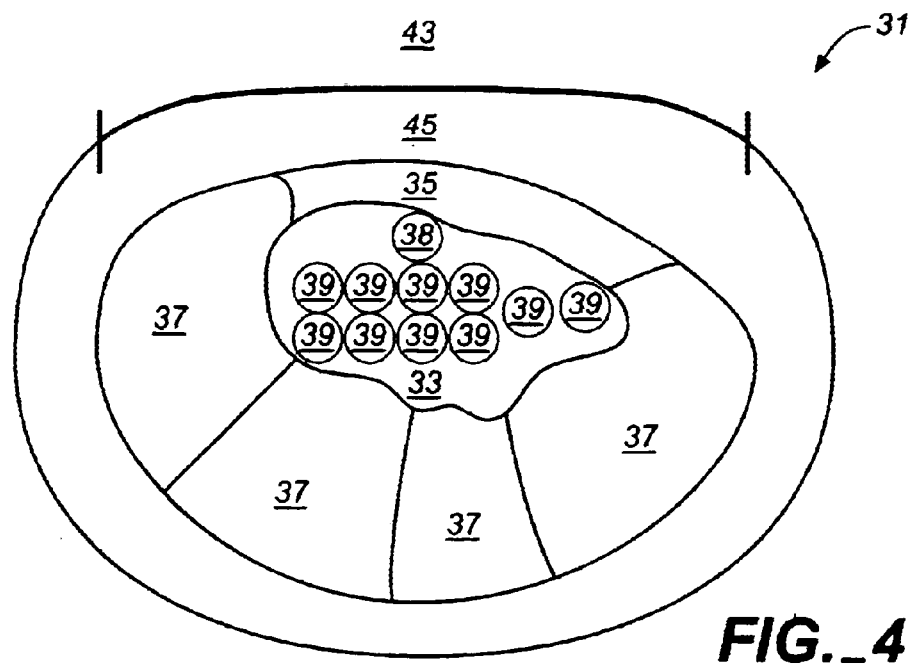
FIG._4
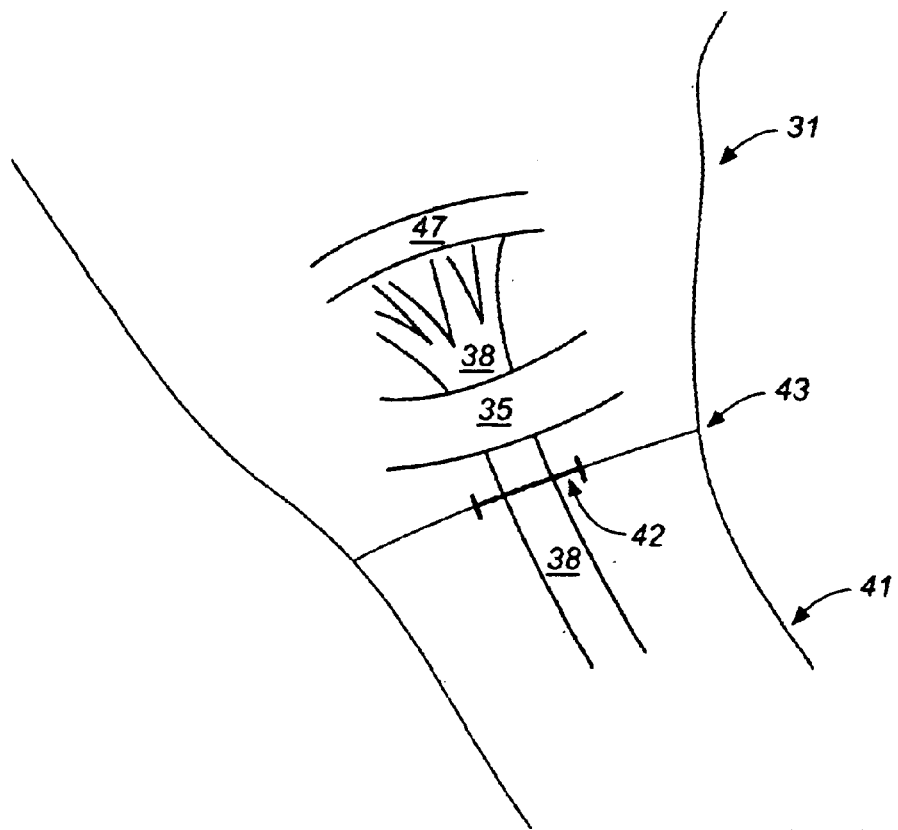
FIG._5

SCALPEL SYSTEM FOR TREATING CARPAL TUNNEL SYNDROME

BACKGROUND OF THE INVENTION

The present invention relates to a specialized scalpel. In particular, the scalpel is used in surgery to relieve pain in the carpal tunnel at the wrist.

People who perform repetitive motions or sustain vibratory stresses are susceptible to carpal tunnel syndrome. Carpal tunnel syndrome is caused by the compression of the nerves and tendons in the palm and wrist of the hands. Patients suffering from carpal tunnel syndrome report pain and numbness in the wrist, hand, and forearms, particularly at night. Treatments to relieve the pain of carpal tunnel syndrome include exercise, wrist splinting, steroid injection, rest, workplace alteration, anti-inflammatory agents, and correction of metabolic disorders. However, in some patients, surgical decompression of the carpal tunnel may be required to relieve the pain. To relieve the pain caused by carpal tunnel syndrome, the transverse carpal ligament that goes over the wrist, also known as the flexor retinaculum, just proximal to the palm, is transected. Prior to the transection of the transverse carpal ligament, a surgical incision is made into the palm of the hand, which causes a scar. The surgical incision on the palm may result in many potential complications, such as injuries, pain and swelling, and increased time for recovery.

Different surgical procedures and devices exist for carpal tunnel release surgery. Strickland, U.S. Pat. No. 5,387,222, discloses a carpal tunnel tome with a slender handle with a blade at one end for use in carpal tunnel release surgery. A pair of relatively blunt protuberances bounds the blade and prevents damage of surrounding tissues during the cutting procedure of the ligament. To access the ligament, a relatively short incision is made in the patient's palm adjacent the distal edge of the transverse carpal ligament, also known as the flexor retinaculum. The incision and tissue are retracted to expose the distal portion of the transverse carpal ligament near the palm. The tome is advanced from the distal to proximal (i.e., palm to wrist), which allows visualization of the ligament. However, the distal to proximal incision is against the direction of the median nerve branching, so that there may be complications, such as laceration of the main trunk of the median nerve. In addition, the surgical procedure requires more than one instrument or a package consisting of retractors, elevators, and other surgical instruments.

A proximal to distal procedure, which avoids some of the disadvantages of Strickland's distal to proximal procedure, is described in Pagnanelli et al., "Carpal tunnel syndrome: surgical treatment using the Paine retinaculatome", J. Neurosurg 75: 77–81, July 1991. The surgery in Pagnanelli et al. is performed with a Paine retinaculatome, in which the knife edge of the retinaculatome extends from the flat portion of the knife in a perpendicular fashion. See id. at 78, FIG. 1. The knife has a concave leading edge with a hook and a blunt trailing edge. See id. at 78, FIG. 1, upper. The surgery begins with a small transverse incision in the distal wrist crease. See id. at 78. Tissue is spread and retracted to expose the underlying median nerve. See id. "The retinaculum is cut a few millimeters down into the palm and up the wrist to allow easy placement of the retinaculatome." See id. at 78–79. This easy placement is achieved by means of a hook on the Paine retinaculatome, which is latched onto the flexor retinaculum ligament, also known as the transverse carpal ligament. The base of the knife is positioned under the ligament and above the nerve, slightly slanted about 20°. See id. at 79. The leading edge of the knife cuts the carpal ligament as the retinaculatome is advanced into the palm. A very characteristic grating sound is produced by division of the ligament. See id.

SUMMARY OF THE INVENTION

The present invention concerns a specialized scalpel for relieving carpal tunnel syndrome. The specialized scalpel has an elongated member including a first portion for handling and a second portion. The second portion has a first surface, a second surface, and a blade on the first surface. The blade has a trailing edge and a sharp, convex leading edge. The leading edge rises gradually at a first angle with respect to the first surface so that when the leading edge is pushed against tissue to make an incision, damage to the surrounding tissue is reduced. The first angle is less than 90 degrees. In one embodiment, the specialized scalpel preferably has several features to reduce damage to the tissue, such as protective flanges, a flat bottom, and a curved front edge.

The specialized scalpel can be used in surgery to release the carpal tunnel in the hand. In carpal tunnel release surgery, a transverse incision is made in the patient's distal wrist crease between the hand and the arm with a surgical instrument. The surgical instrument is positioned below the transverse carpal ligament and advanced in a closed procedure toward the patient's fingertips until the transverse carpal ligament, also known as the flexor retinaculum, is completely transected. The surgical method can be performed with different surgical instruments. The specialized scalpel described above is particularly suited to the present surgical method, as it facilitates the surgical method with a curved front edge, a flat bottom, and a curved leading edge of the knife.

An advantage of the present invention is the prevention of damage by the use of the scalpel in surgery. The gentle slope of the leading edge facilitates ease of advancement of the blade in a closed, percutaneous resection within the carpal tunnel. The curved front edge displaces neurovascular structures and minimizes the likelihood of laceration. The flat bottom helps the knife glide over nerves and tendons and displace surrounding structures away from the blade.

Additionally, the proximal to distal procedure eliminates the need for an incision on the palm and results in a less conspicuous scar. Thus, pain and swelling are minimized, and recovery is expedited.

An additional advantage of the present invention is the use of the specialized scalpel in a partially closed, percutaneous procedure. The scalpel is introduced below the transverse carpal ligament after exposing the surrounding tissue and neurovascular structures. The tissue is not fully exposed by this procedure, and the risk of infection is thereby decreased. Complications of loss of function, pain, and scar tissue formation are also minimized. The partially closed, percutaneous procedure promotes faster healing.

BRIEF DESCRIPTION OF THE DRAWINGS

The above and other features and aspects of the present invention will become more apparent upon reading the following detailed description in conjunction with the accompanying drawings, in which:

FIG. 1 is a side view of the specialized scalpel;

FIG. 2 is a side view of an alternative embodiment of the scalpel;

FIG. 3 is a side view of the front edge of the knife and the attached blade of the scalpel of FIG. 1;

FIG. 4 is a cross-sectional illustration of a patient's hand; and

FIG. 5 is a top view of a patient's hand and arm.

DETAILED DESCRIPTION

FIG. 1 shows a preferred embodiment of the specialized scalpel. The scalpel 11 is elongated and has two parts, a first portion for handling 13 and a second portion 15. The first portion 13 is shown as extending along the same axis as the second portion 15. However, the invention encompasses embodiments, such as in FIG. 2, in which the first portion 13 is at an angle with respect to the second portion 15. The first portion 13 is preferably made of a material that includes plastic.

The second portion 15 has a first surface 17, a second surface 19, and a blade 21 on the first surface 17. The blade 21 is pointed upwards. Directional qualifiers, such as "upward," are in reference to this reference frame. If the blade is oriented other than upwards, orientations and directional qualifiers such as "upward" of other parts will correspond to the new frame of reference. The second portion has a front end 23. The front end 23 preferably is curvilinear and curves upwards relative to the first surface 17. FIG. 3 shows that the curved front end 23 is slightly tipped upward. The curved front end 23 of the scalpel displaces neurovascular structures and minimizes the likelihood of laceration. The second surface 19 is preferably flat. The flat second surface 19 protects the nerves as the knife glides over the nerves and displaces surrounding structures away from the blade 21.

The blade 21 is shaped like a shark's fin and is preferably made of a material such as steel. The height of the blade is designed to minimize damage to the tissue and structures surrounding the ligament being cut in surgery. For example, in carpal tunnel release surgery, the height of the blade is selected to be approximately equivalent to the height of the ligament being cut to prevent cutting of tissue and structures overlying the ligament. In one embodiment, the height of the blade is from about 3.5 mm to about 5 mm.

The blade 21 has a convex leading edge 25 and a trailing edge 27. The leading edge 25 is sharp and rises gradually at a first angle 26 with respect to the first surface 17. The first angle 26 is less than ninety degrees, preferably between approximately 30 degrees and approximately 40 degrees. The gradually sloping leading edge 25 reduces damage to surrounding tissue when it is pushed against the tissue to make an incision. The leading edge 25 preferably has a curvilinear shape, which facilitates the cutting of the transverse carpal ligament. The trailing edge 27 is blunt and rises at a second angle 28 with respect to the first surface 17. The second angle 28 is between zero and ninety degrees, preferably between about 70 degrees and about 80 degrees and most preferably at or close to ninety degrees.

Two protective flanges 29, as shown in FIG. 3, connect the blade 21 to the first surface 17. The protective flanges 29 push away tissue to help the surgeon glide along the tissue. The flanges 29 are preferably made of a material such as epoxy. The epoxy is heated around the blade 21 until the blade 21 is molded into the first surface 17.

The scalpel 11 or other surgical instruments, such as the Paine retinaculatome, can be used in surgery to release the carpal tunnel in the hand. FIG. 4 is a cross-sectional illustration of a patient's hand. The hand 31 has a carpal tunnel 33 surrounded by the transverse carpal ligament 35, also known as the flexor retinaculum, and bones 37. The carpal tunnel 33 includes a median nerve 38 and tendons 39.

FIG. 5 is a top view of a patient's hand and arm. In carpal tunnel release surgery, a transverse incision 42 of approximately one to two centimeters is made with the scalpel 11 in the patient's distal wrist crease 43 between the hand 31 and the arm 41. Neurovascular structures 45 above the transverse carpal ligament 35 can be moved out of the way. The transverse carpal ligament 35 is partially visualized, and identification of the median nerve 38 can be made. The scalpel 11 is then introduced below the transverse carpal ligament 35, which is above the median nerve 38. The blade 21 of the scalpel 11 is facing the transverse carpal ligament 35. A cut is made through the transverse carpal ligament 35, and the scalpel continues to cut the transverse carpal ligament 35 in a proximal to distal direction, i.e., from the patient's wrist towards the patient's fingertips, until the transverse carpal ligament 35 is completely resected. The procedure is a partially closed procedure in that the tissue is not completely exposed. The partially closed procedure decreases the risk of infection. The procedure also eliminates the need for an incision on the palm and results in a less conspicuous scar.

Since the surgical procedure is a relatively closed, percutaneous procedure, there exists potential for tissue damage, especially the arch 47 in carpal tunnel release surgery. It is important to have markings 16 in centimeters on the second portion 15, as shown in FIG. 1. The risk of accidental laceration of the arch 47 is offset by the distance between the end of the ligament and the arch 47 in the middle of the palm. The shield of the design will also protect the arch 47.

It is to be understood that while the invention has been described above in conjunction with specific embodiments, the description and examples are intended to illustrate and not limit the scope of the invention, which is defined by the scope of the appended claims.

What is claimed is:

1. A surgical instrument for relieving carpal tunnel syndrome, comprising:

an elongated member comprising a first portion for handling and a second portion, wherein said second portion includes a first surface, a second surface, and a blade on the first surface, the second portion having a front end; and said blade comprising a leading edge and a trailing edge, wherein said leading edge is sharp, convex, and rises gradually at a first angle with respect to said first surface, said first angle being less than 90 degrees, so that when the leading edge is pushed against tissue to make an incision, damage to surrounding tissue is reduced, wherein the front end of the second portion curves upwards relative to the first surface.

2. The surgical instrument of claim 1, wherein said leading edge has a curvilinear shape.

3. The surgical instrument of claim 1, wherein said first angle is between about 30 degrees and about 40 degrees.

4. The surgical instrument of claim 1, wherein said trailing edge of the blade rises at a ninety degree angle with respect to said first surface.

5. The surgical instrument of claim 1, wherein said trailing edge of said blade rises at a second angle that is less than ninety degrees with respect to said first surface.

6. The surgical instrument of claim 5, wherein said second angle is between about 70 degrees and about 80 degrees.

7. The surgical instrument of claim 1, wherein said blade has a height selected so that when the leading edge is cutting a ligament, damage to the surrounding tissue is reduced.

8. The surgical instrument of claim 1, wherein said blade has a height of about 3.5 mm to about 5 mm.

9. The surgical instrument of claim 1, wherein said blade has protective flanges, said flanges connecting the blade to the first surface of the second portion.

10. The surgical instrument of claim 1, wherein said second surface of the second portion is flat.

11. The surgical instrument of claim 1, wherein said second portion has a curvilinear front end.

12. The surgical instrument of claim 1, wherein the leading edge of the blade is located near but spaced from the front end.

13. The surgical instrument of claim 1, wherein the leading edge has a curvilinear shape, the second surface of the second portion is flat, the second portion has a curvilinear front end, and said front end is curved upward relative to the first surface.

14. The instrument of claim 1, wherein the second portion is elongated and includes markings alone its length for indicating distance of incision.

15. The instrument of claim 1, the first and second portion extending along the same axis.

16. A method of performing carpal tunnel release surgery comprising:
providing a surgical instrument;
making a transverse incision in the patient's distal wrist area using said surgical instrument;
positioning said surgical instrument adjacent the transverse carpal ligament; and
advancing said surgical instrument in a closed, percutaneous resection procedure toward the patient's fingertips until the transverse carpal ligament is completely transected.

17. The method of claim 16, wherein said providing comprises providing a surgical instrument having a first portion for handling and a second portion, wherein said second portion includes a first surface, a second surface, and a blade on the first surface; and a blade comprising a leading edge and a trailing edge, wherein said leading edge is sharp, convex, and rises gradually at a first angle with respect to said first surface, said first angle being less than ninety degrees, so that when the leading edge is pushed against tissue to make an incision, damage to the surrounding tissue is reduced.

18. The method of claim 16, wherein the incision made is between about one centimeter and about two centimeters.

19. The method of claim 17, wherein said providing a surgical instrument includes providing a surgical instrument having a leading edge with a curvilinear shape, a second surface of the second portion being flat, and a second portion with a curvilinear front end, said front end curving upwards relative to said first surface.

20. The method of claim 16, further comprising partially visualizing the ligament and identifying the median nerve prior to positioning the instrument.

21. The method of claim 16, said surgical instrument comprising a portion that includes a first surface and a blade on the first surface, the portion having a front end, said blade comprising a leading edge located near but spaced from the front end, wherein said advancing causes the leading edge to be pushed against the ligament to make an incision, wherein the front end of the second portion curves upwards relative to the first surface, so that the front end displaces neurovascular structures before the arrival of the blade during the advancing to reduce damage to surrounding tissue.

22. The method of claim 16, said surgical instrument comprising an elongated portion that includes markings along its length for indicating distance, said method further including using said markings to reduce risk of accidental laceration of an arch of the patient.

23. The method of claim 22, said method further including using said markings to reduce risk of accidental laceration of the arch of the patient.

* * * * *